United States Patent
Oakley et al.

(10) Patent No.: US 10,137,249 B2
(45) Date of Patent: Nov. 27, 2018

(54) PRIMING CONFIGURATION FOR A MEDICAL DEVICE AND DRUG DELIVERY DEVICE COMPRISING A PRIMING CONFIGURATION

(71) Applicant: Sanofi, Paris (FR)

(72) Inventors: Tom Oakley, Cambridge (GB); Matt Schumann, Bourn (GB); Stuart Milne, Buckden St. Neots (GB)

(73) Assignee: Sanofi, Paris (FR)

( * ) Notice: Subject to any disclaimer, the term of this patent is extended or adjusted under 35 U.S.C. 154(b) by 80 days.

(21) Appl. No.: 14/904,746

(22) PCT Filed: Jul. 17, 2014

(86) PCT No.: PCT/EP2014/065333
§ 371 (c)(1),
(2) Date: Jan. 13, 2016

(87) PCT Pub. No.: WO2015/007814
PCT Pub. Date: Jan. 22, 2015

(65) Prior Publication Data
US 2016/0158451 A1 Jun. 9, 2016

(30) Foreign Application Priority Data
Jul. 17, 2013 (EP) ..................................... 13176858

(51) Int. Cl.
*A61M 5/31* (2006.01)
*A61M 11/00* (2006.01)
(Continued)

(52) U.S. Cl.
CPC ........ *A61M 5/3146* (2013.01); *A61M 11/007* (2014.02); *A61M 5/1452* (2013.01);
(Continued)

(58) Field of Classification Search
CPC ........ A61M 5/3146; A61M 2005/1402; A61M 5/31511; A61M 5/31515; A61M 5/1452
See application file for complete search history.

(56) References Cited

U.S. PATENT DOCUMENTS 3,494,358 A * 2/1970 Duesterheft ............ A61M 5/20
604/137
2005/0085776 A1 * 4/2005 Hommann ........ A61M 5/31553
604/207
(Continued)

FOREIGN PATENT DOCUMENTS

JP H9-507416 7/1997
JP 2010/073452 4/2010
(Continued)

OTHER PUBLICATIONS

Rote Liste, "50. Hypophysen-, Hypothalamushormone, andere regulatorische Peptide u. ihre Hemmstoffe," Chapter 50, ed. 2008, 20 pages.
(Continued)

*Primary Examiner* — Rebecca E Eisenberg
*Assistant Examiner* — Courtney Fredrickson
(74) *Attorney, Agent, or Firm* — Fish & Richardson P.C.

(57) ABSTRACT

The priming configuration comprises a piston rod (1), a bung (2), which is provided to be driven by the piston rod, and a movable element (5), which is engaged with the piston rod. The movable element is arranged to be movable in a predefined direction (10) with respect to the piston rod by a user of the drug delivery device. A movement of the movable element in the predefined direction advances the piston rod in a further direction (11), providing a priming of the drug delivery device before use. The predefined direction may especially be transverse to the further direction, and the further direction may especially be directed from the piston rod towards the bung (2). A gap (12) or clearance between the piston rod (1) and the bung (2) can thus be removed, and the stiction of the bung (2) to the cartridge (3) can be reduced.

21 Claims, 1 Drawing Sheet

(51) Int. Cl.
A61M 5/315 (2006.01)
A61M 15/00 (2006.01)
A61M 5/145 (2006.01)
A61M 5/14 (2006.01)

(52) U.S. Cl.
CPC ..... *A61M 5/31511* (2013.01); *A61M 5/31515* (2013.01); *A61M 5/31583* (2013.01); *A61M 15/009* (2013.01); *A61M 2005/1402* (2013.01)

(56) References Cited

U.S. PATENT DOCUMENTS

2012/0283645 A1 11/2012 Veasey et al.
2015/0343145 A1 12/2015 Nzike et al.

FOREIGN PATENT DOCUMENTS

| JP | 2012-231932 | 11/2012 |
| JP | 2013/506463 | 2/2013 |
| JP | 2015-531287 | 11/2015 |
| WO | WO 95/19194 | 7/1995 |
| WO | WO 2007/066152 | 6/2007 |
| WO | WO 2010/139639 | 12/2010 |
| WO | WO 2011/039231 | 4/2011 |

OTHER PUBLICATIONS

International Preliminary Report on Patentability in International Application No. PCT/EP2014/065333, dated Jan. 19, 2016, 8 pages.
International Search Report and Written Opinion in International Application No. PCT/EP2014/065333, dated Sep. 26, 2014, 10 pages.

\* cited by examiner

PRIMING CONFIGURATION FOR A MEDICAL DEVICE AND DRUG DELIVERY DEVICE COMPRISING A PRIMING CONFIGURATION

CROSS-REFERENCE TO RELATED APPLICATIONS

This application is a U.S. national stage application under 35 USC § 371 of International Application No. PCT/EP2014/065333, filed on Jul. 17, 2014, which claims priority to European Patent Application No. 13176858.2, filed on Jul. 17, 2013, the entire contents of which are incorporated herein by reference.

Drug delivery devices, in particular pen-type injection devices, comprise a bung, which serves to eject doses of a drug from a container and may be provided as part of a drug cartridge, and a piston rod driving the bung. The piston rod may be provided with a bearing to facilitate a relative movement of the piston rod with respect to the bung. The drug delivery device may be provided with a mechanism for setting a dose and for advancing the piston rod to deliver the dose set.

At the end of the assembly of the device a gap may intentionally be left between the end of the piston rod and the bung. The gap is a consequence of the tolerances associated with the assembled parts and of the desire not to pre-load the bung in the assembled device before the first usage takes place.

When the device is used for the first time, the dose actually delivered is liable to be less than the dose set, and the difference equals the volume that would be ejected if the bung were travelling simultaneously with the piston rod even before the piston rod gets into contact with the bung. This may cause the first dose to be well outside the allowable accuracy limits.

The user is therefore instructed to perform a priming step like the ejection of 'air shot' prime doses until fluid begins to be ejected. Priming is such an act of preparing the device for first use. Except for a removal of any clearances and tolerances in the device, priming may be required to overcome a static friction or 'stiction' of parts occurring when the device has not been used for some time, in particular for the time between manufacture and first use. The bung tends to stick to the cartridge, for instance, and moving the bung for the first time usually requires a greater force than on subsequent shots.

Sub-lingual spray devices are sometimes based on mechanical pumps which aerosolise a liquid medicament. The pump needs to be primed before use to ensure that the metering chamber is full.

Metered dose inhalers typically feature a metering chamber which may contain fluid (liquid, possibly with suspended particles, or gas, or a mixture of said liquids and gases). The fluid may be at the same pressure as ambient pressure or different. It is sometimes advantageous to prime the metered dose inhaler such that the metering chamber contains an acceptable mass of an acceptable fluid or mixture of fluids, and at an acceptable pressure for subsequent use in drug delivery.

It is an object of the present invention to provide an easy way of priming a medical device, in particular a drug delivery device comprising a piston rod that is provided to drive a bung for expelling a drug from a container like a cartridge.

This object is achieved with the priming configuration according to claim 1 and with the drug delivery device according to claim 14. Further embodiments and variants derive from the dependent claims.

A piston rod according to this invention shall mean any member that is intended to drive a piston or bung of a drug delivery device and may particularly be a lead screw.

The term "drug", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39), des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Trp(O2)25] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The priming configuration comprises a movable functional part provided for an operation of the device, and a movable element or exerciser operationally coupled with the functional part. The movable element is arranged to be movable in a predefined direction with respect to the functional part by a user of the medical device, a movement of the movable element in the predefined direction advancing the functional part in a further direction thereby providing a priming of the medical device before use.

The priming may be any operation putting the device in condition for ready use. It may especially comprise a removal of any clearances or tolerances between parts of the device and may be adapted to put components of the device into suitable compression or tension, for example. It may also comprise a movement of a mechanical part to overcome a stiction caused when the device is not used for a significant period of time, particularly between manufacture and first use. It may also comprise the removal of gas such as air from the drug container and/or needle. It may also comprise the ejection of drug from the device.

The priming configuration may be used in a variety of medical devices, including drug delivery devices or sublingual spray devices or metered dose inhalers, for instance. The priming configuration of a drug delivery device especially comprises a movable element or exerciser, which allows the drug delivery device to be completely and reliably primed for first use in one easy step of operation. The movable element serves to generate a slight movement of the piston rod in the direction towards the bung to take up any manufacturing tolerances. Instead or additionally, the movable element may generate a slight movement of the bung to overcome the stiction from long-term storage. Instead or additionally, the movable element may change the mass or mixture of fluids in a metering chamber, or change the pressure in a metering chamber. The movable element may especially be a removable element, which is removed from the device after the priming step. In particular, the priming configuration may be a piston rod arrangement for priming a drug delivery device, and the movable functional part may be a piston rod.

The priming configuration is especially advantageous in drug delivery devices using a spring to move the bung. The spring must otherwise provide enough force or torque to overcome the initial stiction force, even when the user sets only the minimum dose. Therefore the spring has to provide greater force and/or torque than would be necessary if it did not have to overcome the stiction. Therefore, one or more components may be subjected to greater force and/or torque, which may require materials and/or component design to avoid failures due to deflection, yield, creep or fatigue. This results in larger size and larger mass of the device and increases the device cost. Furthermore the user has to apply a greater torque when selecting a dose. In spring-driven drug delivery devices the priming configuration allows the application of a weaker and smaller driving spring.

In one aspect the invention relates to a priming configuration for a drug delivery device, comprising a piston rod, a bung, which is provided to be driven by the piston rod, and a movable element, which is engaged with the piston rod. The movable element is arranged to be movable in a predefined direction with respect to the piston rod by a user of the drug delivery device. A movement of the movable element in the predefined direction advances the piston rod in a further direction. The predefined direction may especially be transverse to the further direction, and the further direction may especially be directed from the piston rod towards the bung. The advancement of the piston rod does not belong to the regular use of the device and is not intended for selecting or delivering a dose, but only provides a priming of the drug delivery device before use.

In an embodiment of the priming configuration the movable element is engaged with the piston rod by making a contact with the piston rod in an inclined surface of the movable element. The inclined surface is inclined with respect to the further direction and is in contact with the piston rod. This has the advantage of an easy construction, because the arrangement of the contact surface between the piston rod and the movable element suffices to advance the piston rod by a movement of the movable element.

A further embodiment of the priming configuration further comprises an opening in the piston rod, the movable element extending into the opening and being engaged with the piston rod within the opening. This has the advantage that the operational coupling with the movable element may be arranged at the axial centre of the piston rod and at various positions along the piston rod.

A further embodiment of the priming configuration further comprises a grip of the movable element, the grip being provided to move the movable element in the predefined direction away from the piston rod. This has the advantage that the movable element may thus be removed from the device.

A further embodiment of the priming configuration further comprises a button of the movable element, the button being provided to move the movable element in the predefined direction towards the piston rod. This has the advantage that the movable element may be provided as an operation button on the device.

The movable element may be provided to be removed from the piston rod, especially to be completely removed from the drug delivery device. This has the advantage that the movable element, which is only used once, does not interfere with the further use of the device and that it may be seen from the outer appearance of the device whether the priming step has already been performed.

In a further embodiment of the priming configuration, the functional part is in communication with a mechanical pump.

In a further embodiment of the priming configuration, the functional part is in communication with a metering chamber.

In another aspect the invention relates to a drug delivery device comprising such a priming configuration. The drug delivery device may especially be an injection device and/or a pen-type device. The priming configuration is especially suitable for drug delivery devices, because it allows easy manufacture of the device and easy priming to remove any manufacturing tolerances.

The following is a detailed description of embodiments of the priming configuration in conjunction with the appended drawings.

Figure 1:
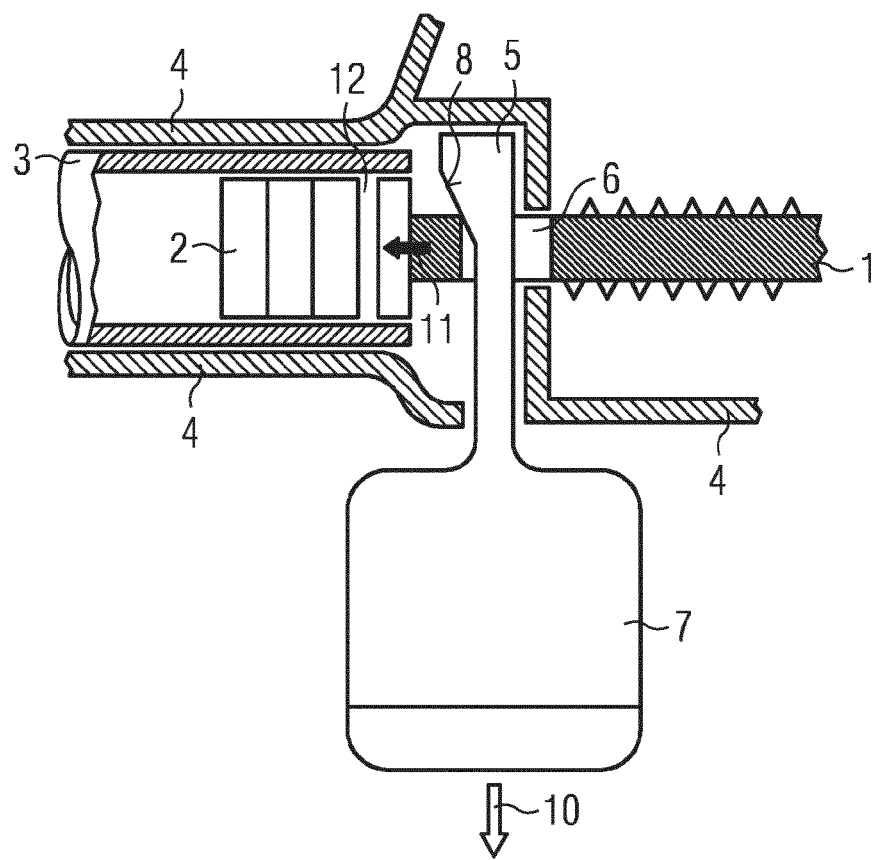
FIG. 1 is a cross section of an embodiment of the priming configuration.

FIG. 1 is a cross section of an embodiment of the priming configuration in which the movable element or exerciser is implemented as a 'pull-tab'. The piston rod 1 may already be in contact with the bung 2, or the piston rod 1 may instead be arranged at a very small distance from the bung 2, as shown in the example of FIG. 1. The bung 2 may be provided in a cartridge 3, which contains a drug. The cartridge 3 may be inserted in a body 4 or housing of a drug delivery device. Instead of a cartridge 3, any drug container or receptacle may be provided, and the bung 2 may be arranged within the container at a position suitable for expelling the drug. The small gap 12 between the piston rod 1 and the bung 2 may be a clearance that is due to assembly tolerances or the like. This gap 12 is to be removed by a priming step, and a possible stiction of the bung 2 at the inner side walls of the cartridge 3 or container is to be overcome. The movable element 5 is engaged with the piston rod 1 and is provided with some kind of operation element like a tab or grip 7, which may be arranged, in particular at or near a surface of a body 4 or extending out of a body 4, in such a fashion that a user can pull the movable element 5 in the predefined direction 10 away from the piston rod 1. The act of pulling the tab or grip 7 moves the piston rod 1 in the further direction 11 into contact with the bung 2, thus removing the clearance due to manufacturing tolerances. The movement of the piston rod 1 may be continued to reduce the stiction of the bung 2 by a slight movement of the bung 2 relative to the cartridge 3 or container. The movement of the piston rod 1 may be continued to expel some or all gas from the drug container 3 and/or needle (not shown). The movement of the piston rod 1 may be continued to expel some drug from the drug delivery device.

The transmission of the movement of the movable element 5 into a movement of the piston rod 1 may be effected by an inclined surface 8 of the movable element 5 engaging the piston rod 1. In the embodiment according to FIG. 1, the movable element 5 extends into an opening 6 of the piston rod 1, and the inclined surface 8 is in contact with the piston rod 1 within the opening 6. The inclined surface 8 may be formed by a widening of the part of the movable element 5 that extends into the opening 6. When the movable element 5 is pulled in the predefined direction 10 the inclined surface 8 slides on an inner rim of the opening 6 and pushes the piston rod 1 in the further direction 11 towards the bung 2. In this case the predefined direction 10 is essentially transverse to the further direction 11. The movable element 5 may be intended to be left in the device after priming, and in this case it may be formed as a feature created from the body 4 or another component of the device. The movable element 5 may instead be intended to be completely removed from the device in the course of the priming step.

Figure 2:
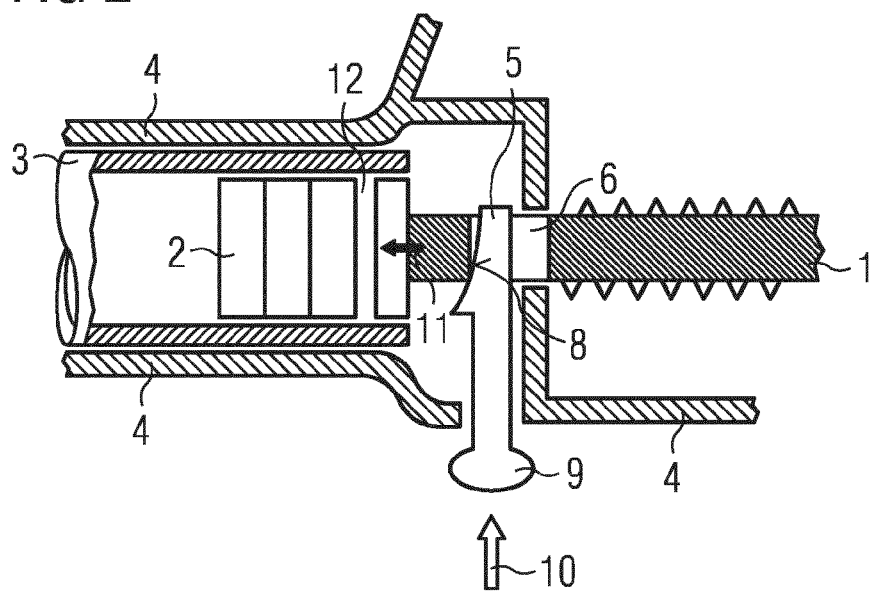
FIG. 2 is a cross section of a further embodiment of the priming configuration.

FIG. 2 is a cross section of a further embodiment of the priming configuration in which the movable element or exerciser is implemented as a button. The elements of the embodiment according to FIG. 2 that are similar to elements of the embodiment according to FIG. 1 are designated with the same reference numerals. The movable element 5 comprising the button 9 may be formed as a separate component of the device, or it may be a feature created from the body 4 or another component. In order to prime the device the user presses the button 9 to push the movable element 5 in the predefined direction 10, which is towards the piston rod 1 in this embodiment. The act of pressing the button 9 moves the piston rod 1 in the further direction 11 into contact with the bung 2, and the bung 2 may also be moved slightly relative to the cartridge 3 or container to reduce the stiction of the bung 2. The movement of the piston rod 1 may be continued to expel some or all gas from the drug container 3 and/or needle (not shown). The movement of the piston rod 1 may be continued to expel some drug from the drug delivery device.

The transmission of the movement of the movable element 5 into a movement of the piston rod 1 may be effected by an inclined surface 8 of the movable element 5 engaging the piston rod 1 in a way similar to the embodiment according to FIG. 1. In the embodiment according to FIG. 2 the movable element 5 also extends into an opening 6 of the piston rod 1, and the inclined surface 8, which may be formed by a tapering of the movable element 5, is in contact with the piston rod 1 within the opening 6. When the movable element 5 is pushed in the predefined direction 10 the inclined surface 8 slides on an inner rim of the opening 6 and pushes the piston rod 1 in the further direction 11 towards the bung 2. In this case the predefined direction 10 is also essentially transverse to the further direction 11. The movable element 5 may be intended to be removed from the device after priming, in order to offer a free passage to the piston rod 1. To this end the button 9 may be formed in such a manner that it can be gripped to pull the movable element 5 out of the body 4. Alternatively, the movable element 5 may remain in the device but be implemented in such a way as not to impede the subsequent function of the piston rod 1.

In other embodiments of the priming configuration, the functional part may be in communication with a mechanical pump or with a metering chamber.

The priming configuration has especially the advantages that it reduces the number of user steps to one push or pull and, in addition, guarantees that the user performs the priming correctly. Another advantage is that it may be made apparent to the user(s) whether or not priming has been performed. A wastage of drug formulation is avoided during priming. Stiction of the bung is effectively reduced. The described priming exerciser is useful in all known designs of drug delivery devices, especially pen-type devices. It may also be applied in sub-lingual spray devices that comprise a mechanical pump rendering an aerosol of a liquid medicament. The pump needs to be primed before use to ensure that the metering chamber is full. It may also be applied to metered dose inhalers that comprise a metering chamber. The priming configuration can be used to ensure that an acceptable mass of an acceptable fluid or mixture of fluids is in the metering chamber and at an acceptable pressure.

REFERENCE NUMERALS

1 piston rod
2 bung
3 cartridge
4 body
5 movable element
6 opening
7 grip
8 inclined surface
9 button
10 direction
11 further direction
12 gap

The invention claimed is:

1. A priming configuration for a medical device, the priming configuration comprising:
   a piston rod configured to operate the device; and
   a movable element comprising an inclined surface being arranged to engage the piston rod, wherein the inclined surface is arranged to be movable in a transverse direction with respect to the piston rod by a user of the medical device, wherein the inclined surface slides along the piston rod during a movement of the inclined surface in the transverse direction, and wherein the movement of the inclined surface in the transverse direction from one end of the inclined surface to an opposite end of the inclined surface causes the engagement of the inclined surface and the piston rod to advance the piston rod in a further direction different from the transverse direction thereby providing a priming of the medical device before use.

2. The priming configuration of claim 1, wherein the priming configuration is a piston rod arrangement for priming a drug delivery device.

3. The priming configuration according to claim 2, wherein the inclined surface is inclined with respect to the further direction and is in contact with the piston rod.

4. The priming configuration according to claim 2, further comprising:
   a through opening in the piston rod, the movable element extending into the through opening and being engaged with the piston rod within the opening.

5. The priming configuration according to claim 2, further comprising:
   a grip of the movable element, the grip configured to move the movable element in a predefined direction, and wherein the predefined direction is a direction away from the piston rod.

6. The priming configuration according to claim 2, further comprising: a button of the movable element, the button configured to move the movable element in a predefined direction, and wherein the predefined direction is a direction towards the piston rod.

7. The priming configuration according to claim 2, wherein the movable element is configured to be removed from the piston rod.

8. The priming configuration of claim 1, wherein the piston rod is configured to drive a bung of a container containing a drug in a drug delivery device.

9. The priming configuration of claim 8, wherein the priming includes a slight movement of the bung generated by the movable element to overcome a stiction of the bung to the container.

10. The priming configuration of claim 8, further comprising:
    a spring configured to move the bung, the spring advancing the piston rod in the further direction thereby providing the priming.

11. The priming configuration according to claim 8, wherein the further direction is from the piston rod towards the bung.

12. The priming configuration of claim 1, wherein the piston rod is in communication with a mechanical pump.

13. The priming configuration of claim 1, wherein the piston rod is in communication with a metering chamber.

14. A drug delivery device comprising: a priming configuration comprising: a movable piston rod configured to operate the drug delivery device; and a movable element comprising an inclined surface and a tab, the inclined surface being arranged to engage the piston rod, wherein the inclined surface is arranged to incline in a direction of drug delivery during an operation of the drug delivery device, a movement of the tab in a transverse direction causes the engagement between the inclined surface and the piston rod to advance the piston rod in a further direction thereby providing a priming of the drug delivery device before use.

15. The drug delivery device of claim 14, wherein the drug delivery device is an injection device.

16. The drug delivery device of claim 14, wherein the drug delivery device is a pen-type device.

17. The drug delivery device of claim 14, wherein the priming configuration is a piston rod arrangement for priming the drug delivery device.

18. The drug delivery device of claim 14, wherein the piston rod is configured to drive a bung of a container containing a drug in the drug delivery device.

19. The drug delivery device of claim 18, wherein the priming includes a slight movement of the bung generated by the movable element to overcome a stiction of the bung to the container.

20. The drug delivery device of claim 18, wherein the priming configuration further comprises:
    a spring configured to move the bung, the spring advancing the piston rod in the further direction thereby providing further priming.

21. A drug delivery device comprising: a priming configuration comprising: a piston rod configured to operate the drug delivery device; a movable element comprising an inclined surface being arranged to contact the piston rod and a tab, the movable element being operationally coupled with the piston rod, wherein the tab is arranged to be movable in a transverse direction with respect to the piston rod by a user of the drug delivery device, wherein the inclined surface slides along the piston rod during a movement of the tab in the transverse direction, and wherein, in response to the movement in the transverse direction, the piston rod is advanced in a further direction different from the transverse direction thereby providing a priming of the drug delivery device before use; and a through opening in the piston rod, the movable element extending into the through opening and being engaged with the piston rod within the opening.

* * * * *